US006942672B2

(12) United States Patent
Heilman et al.

(10) Patent No.: US 6,942,672 B2
(45) Date of Patent: Sep. 13, 2005

(54) METHOD AND APPARATUS FOR ATTACHING A CONDUIT TO THE HEART OR A BLOOD VESSEL

(75) Inventors: Marlin Stephen Heilman, Sarver, PA (US); Richard Andrew Sofranko, Pittsburgh, PA (US); Carl Michael Parisi, Kittaning, PA (US)

(73) Assignee: Vascor, Inc., Pittsburgh, PA (US)

( * ) Notice: Subject to any disclaimer, the term of this patent is extended or adjusted under 35 U.S.C. 154(b) by 285 days.

(21) Appl. No.: 10/047,507

(22) Filed: Oct. 23, 2001

(65) Prior Publication Data

US 2003/0078592 A1 Apr. 24, 2003

(51) Int. Cl.[7] .............................................. A61F 11/00
(52) U.S. Cl. ..................................................... 606/108
(58) Field of Search ................................ 606/108, 110, 606/111, 113, 114, 115, 158, 167, 170, 181, 182, 183; 128/850, 856; 604/101.01, 103.03, 163, 164.01, 164.04

(56) References Cited

U.S. PATENT DOCUMENTS

| 2,835,253 | A | * | 5/1958 | Borgeson ........................ 606/1 |
|---|---|---|---|---|
| 4,366,819 | A | | 1/1983 | Kaster |
| 4,503,568 | A | | 3/1985 | Madras |
| 4,562,597 | A | | 1/1986 | Possis et al. |
| 4,652,265 | A | | 3/1987 | McDougall |
| 4,661,096 | A | | 4/1987 | Teeple |
| 4,808,163 | A | | 2/1989 | Laub |
| 5,078,735 | A | | 1/1992 | Mobin-Uddin |
| 5,089,017 | A | | 2/1992 | Young et al. |
| 5,197,976 | A | | 3/1993 | Herweck et al. |
| 5,211,683 | A | | 5/1993 | Maginot |
| 5,258,042 | A | | 11/1993 | Mehta |
| 5,275,622 | A | | 1/1994 | Lazarus et al. |
| 5,300,015 | A | | 4/1994 | Runge |

(Continued)

OTHER PUBLICATIONS

Thoughts and Progress, Technique for Apex Cannulation without Extracorporeal Circulation, Artif Organs, vol. 11, No. 3, pp. 269–271.

*Primary Examiner*—Kevin Shaver
*Assistant Examiner*—Anuradha Ramana
(74) *Attorney, Agent, or Firm*—Buchanan Ingersoll PC (57) ABSTRACT

An apparatus and method for safely attaching a conduit to the heart, such as a conduit for connection to an implantable blood pump, or to a blood vessel, as in a heart bypass graft, without the need for a cardiopulmonary bypass. The apparatus can include an enclosure attachable to the heart and having sealed within the enclosure at least part of a coring tool and one end of the conduit which will be attached to the heart. A heart attachment member can be affixed to the enclosure for facilitating attachment of the apparatus to the heart and the coring tool can have a cutting member and a member for holding the tissue to be cut from the heart. All air can be evacuated from the enclosure prior to cutting tissue from the heart and attachment of the conduit.

20 Claims, 11 Drawing Sheets

U.S. PATENT DOCUMENTS

| | | | | |
|---|---|---|---|---|
| 5,304,220 A | | 4/1994 | Maginot | |
| 5,348,528 A | | 9/1994 | Vince | |
| 5,419,774 A | * | 5/1995 | Willard et al. | 604/22 |
| 5,425,765 A | | 6/1995 | Tiefenbrun et al. | |
| 5,437,601 A | | 8/1995 | Runge | |
| 5,470,320 A | | 11/1995 | Tiefenbrun et al. | |
| 5,571,167 A | | 11/1996 | Maginot | |
| 5,672,168 A | * | 9/1997 | de la Torre et al. | 606/1 |
| 5,725,357 A | | 3/1998 | Nakazeki et al. | |
| 5,749,375 A | | 5/1998 | Maginot | |
| 5,755,687 A | | 5/1998 | Donlon | |
| 5,813,409 A | * | 9/1998 | Leahy et al. | 128/897 |
| 5,891,159 A | * | 4/1999 | Sherman et al. | 606/144 |
| 5,911,702 A | | 6/1999 | Romley et al. | |
| 5,922,022 A | | 7/1999 | Nash et al. | |
| 5,928,253 A | | 7/1999 | Sherman et al. | |
| 5,941,908 A | | 8/1999 | Goldsteen et al. | |
| 5,944,730 A | | 8/1999 | Nobles et al. | |
| 5,968,089 A | | 10/1999 | Krajicek | |
| 5,972,020 A | | 10/1999 | Carpentier et al. | |
| 5,976,178 A | | 11/1999 | Goldsteen et al. | |
| 6,001,056 A | | 12/1999 | Jassawalla et al. | |
| 6,010,531 A | | 1/2000 | Donlon et al. | |
| 6,024,755 A | | 2/2000 | Addis | |
| 6,030,395 A | | 2/2000 | Nash et al. | |
| 6,036,705 A | | 3/2000 | Nash et al. | |
| 6,042,598 A | | 3/2000 | Tsugita et al. | |
| 6,056,723 A | | 5/2000 | Donlon | |
| 6,056,762 A | | 5/2000 | Nash et al. | |
| 6,063,114 A | | 5/2000 | Nash et al. | |
| 6,077,277 A | * | 6/2000 | Mollenauer et al. | 606/144 |
| 6,086,605 A | | 7/2000 | Barbut et al. | |
| 6,090,097 A | | 7/2000 | Barbut et al. | |
| 6,090,128 A | | 7/2000 | Douglas | |
| 6,117,167 A | | 9/2000 | Goicoechea et al. | |
| 6,123,726 A | | 9/2000 | Mori et al. | |
| 6,152,948 A | | 11/2000 | Addis | |
| 6,168,586 B1 | | 1/2001 | Hahnen | |
| 6,171,319 B1 | | 1/2001 | Nobles et al. | |
| 6,224,620 B1 | | 5/2001 | Maahs | |
| 6,253,768 B1 | | 7/2001 | Wilk | |
| 6,254,564 B1 | | 7/2001 | Wilk et al. | |
| 6,254,578 B1 | | 7/2001 | Grooters et al. | |
| 6,258,021 B1 | | 7/2001 | Wilk | |
| 6,258,069 B1 | | 7/2001 | Carpentier et al. | |
| 6,264,601 B1 | | 7/2001 | Jassawalla et al. | |
| 6,270,513 B1 | | 8/2001 | Tsugita et al. | |
| 6,656,221 B2 | * | 12/2003 | Taylor et al. | 623/2.11 |

* cited by examiner

METHOD AND APPARATUS FOR ATTACHING A CONDUIT TO THE HEART OR A BLOOD VESSEL

BACKGROUND

The invention relates to the attachment of a conduit to the heart, such as a conduit for connection to an implantable blood pump, or for attaching a conduit to a blood vessel, as in a heart bypass graft. Particularly, the method and apparatus according to the invention provides for the safe attachment of a conduit to a ventricle of the heart without the need for performing a normally requisite cardiopulmonary bypass.

Each year hundreds of thousands of patients undergo life saving heart operations which necessitate the use of a heart, i.e., cardiopulmonary, bypass. The cardiopulmonary bypass procedure enables surgeons to perform complex heart operations without the heart actively pumping or, in many instances, not even filled with blood. In its simplest form, the bypass can be thought of as a procedure that provides an alternate blood pathway around the heart to maintain the blood flow through the body's tissues while the heart, which normally provides this function, is being surgically repaired. Typically, persons needing implantation of a left ventricular assist device ("LVAD") require the establishment of a bypass pathway.

During implantation of an LVAD the patient's left ventricle is isolated from the circulatory system so that it may be entered for purposes of installing the LVAD's inflow conduit into the apex of the left ventricle. It is important that this is accomplished without excessive blood loss or air entering the left ventricle and circulation. The patient's circulation is maintained by a separate bypass pump and oxygenator, which temporarily bypasses the left ventricle. Bypassing the heart has a variety of risks to the patient in addition to its related expense. The main hazards surrounding the use of a bypass involve blood damage and embolism to the brain and body. The risk of these hazards tends to increase in proportion to the amount of time the patient is "on bypass". Typically, the outflow conduit of the LVAD is attached to the aorta with an inflow conduit being attached to the left ventricular apex. Attachment of the outflow conduit of the LVAD does not require the cessation of blood flow within the aorta. The LVAD outflow conduit is typically made of a biocompatible fabric, such as polyester, and has a flexible tubular shape that can be attached to the aorta through the use of a side-biting vascular clamp. After the conduit is sewn to the aorta, and the other components connected, the side-biting clamp is released to allow blood to enter the conduit. The attachment of the inflow conduit for the LVAD is more problematic since attachment to the left ventricular apex cannot be accomplished using the vascular connection technique. The inflow conduit of an LVAD typically has a rigid cannula portion which transverses the muscle of the left ventricular apex and is designed to remain open at all times. For the case of a continuous flow pump like the one outlined in U.S. Pat. No. 5,928,131, blockage of the inflow conduit by clamping the left ventricle could cause severe heart tissue and blood damage. Further, the cannula's rigidity prevents the use of a side-biting clamp. Unlike the aortic connection in which a longitudinal incision is made along the clamped arterial wall, attachment of the inflow conduit requires a circular incision be made through the apical ventricular wall. To quickly insert the inflow conduit into the circular ventricular incision would risk induction of an air emboli into the arterial system or excessive blood loss from the opened ventricle.

Accordingly, it can be understood that there is a need for a method and apparatus for safely attaching an inflow conduit of an LVAD to the left ventricular apex of a heart without the necessity for performing the conventionally necessary cardiopulmonary bypass.

SUMMARY

One presently preferred embodiment of the invention provides a method and associated apparatus for attaching a conduit to the heart. In particular, the method and apparatus safely attach the conduit, such as an inflow conduit for an LVAD, to the heart without the need to perform cardiopulmonary bypass. The apparatus can include an enclosure which provides an air-free environment and contains all of the instruments and other components needed to safely remove a plug of tissue from the heart and securely attach the end of the conduit to the heart without performing cardiopulmonary bypass. The members of the apparatus can be provided as integral members of the sealed enclosure, which can be attached to the heart prior to performing the operations needed to attach the conduit to the heart. The enclosure can be evacuated of all air, for example, by filling it with a blood compatible fluid like sterile saline. The enclosure can serve as a barrier to prevent surrounding air from entering the circulatory system during attachment of the conduit. Attachment of the apparatus to the heart can be accomplished using an attachment member which can be affixed to the enclosure prior to attachment to the heart. If the enclosure has a preformed opening, it can be filled with saline, after it is attached to the heart via the attachment member and thus sealed, in order to remove all air from within the enclosure. Alternatively, the enclosure can be pre-sealed and either be pre-filled with saline, or potentially have all air evacuated using a vacuum process, prior to attachment to the heart. In this case, the apparatus would be a pre-packaged unit ready to attach to the heart and would not need to be filled with saline during the attachment procedure. After attachment of the enclosure to the heart, an opening in the heart can be created using a coring tool, of which at least the coring end is sealed within the enclosure. The coring tool can include a cutting member for separation of the core tissue from the heart and a holding member adapted to hold the plug of heart tissue being removed. Where the enclosure is pre-sealed, the coring tool can simply core through both the enclosure and the heart tissue. When the plug of tissue has been fully dissected, the coring tool along with the plug of tissue, and, where the enclosure is pre-sealed, also a portion of the enclosure removed during coring, can be retracted into the enclosure away from the opening in order to make space for the insertion and attachment of the conduit. At least the end of the conduit which will be attached to the heart can be sealed within the enclosure and the opposite end can be closed of in some manner to keep air out of the enclosure. The end of the conduit can then be advanced into the hole created by the coring tool and secured to the heart, normally via the sewing cuff, using a fastening member that can also be provided with the enclosure. The remaining procedure is simply to connect the other end of the conduit, such as to an LVAD, and cut away the enclosure from the inflow conduit and heart attachment member.

Another embodiment can utilize a like method and associated apparatus but for attaching a conduit to a blood vessel. In this case, instead of attaching the conduit between the heart and the LVAD, the conduit would be attached between a blood vessel and the LVAD.

BRIEF DESCRIPTION OF THE FIGURES

A more complete understanding of the invention can be obtained by considering the following detailed description in conjunction with the accompanying drawing figures, in which:

FIG. 3b is a sectional view through line IIIb—IIIb in FIG. 3a.

FIG. 8b is a view taken along line VIIIa—VIIIa in FIG. 8a.

FIG. 9a is a side view of the conduit 24 shown in FIGS. 8a–8b with the tip expanded.

FIG. 9b is a view taken along line IXa—IXa in FIG. 8a.

FIG. 12b is a sectional view of FIG. 12a

DETAILED DESCRIPTION

The apparatus 15 of the present invention is particularly well-suited for safely installing an inflow conduit to the left ventricle without the need for a heart bypass. Essentially, the apparatus 15 provides for attachment of a conduit to the heart in an air-free environment. The apparatus 15 enables an air-free environment by providing a contained and sealed enclosure 27 around the site intended for the conduit 24/graft 25 attachment and all instruments required for complete attachment of the conduit 24 to the heart. Consequently, the apparatus 15 and method eliminates the need for cardiopulmonary bypass, thus eliminating such bypass associated risks as hemolysis and air emboli.

Figure 1:
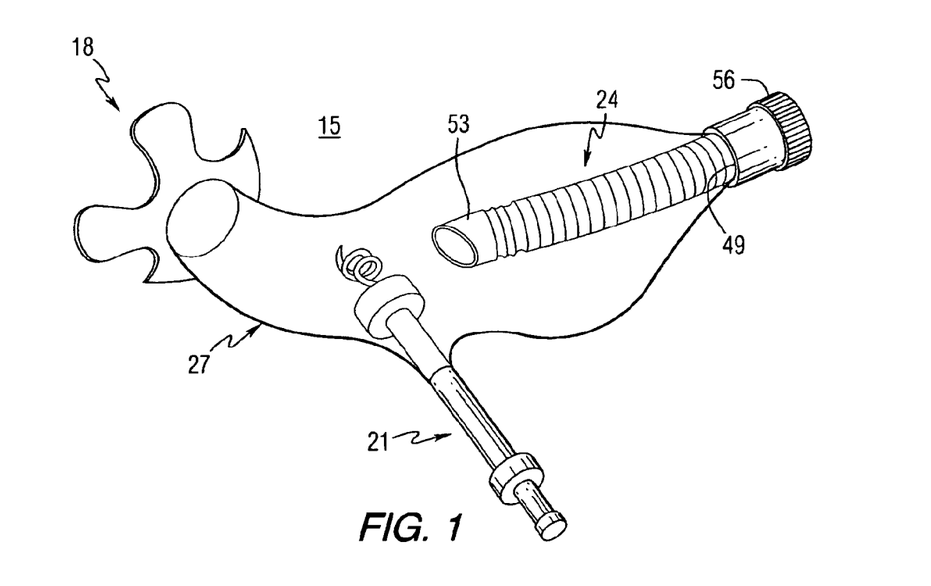
FIG. 1 is a perspective view showing an embodiment of the invention for attaching a conduit to the heart without the need for performing a cardiopulmonary bypass.
Figure 2:
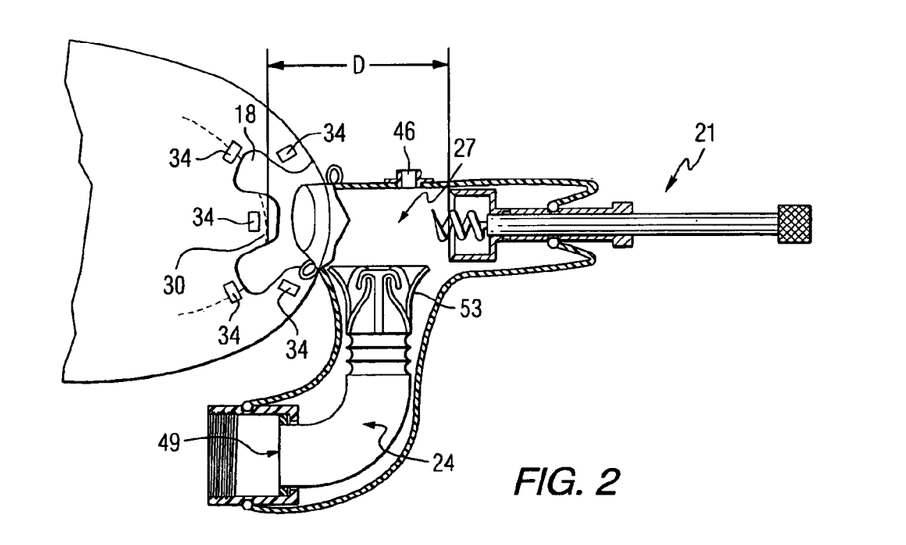
FIG. 2 is a perspective view of an embodiment of the invention similar to that shown in FIG. 1 as it may look attached the heart.

Referring now to FIG. 1, the apparatus 15 can include a heart attachment member, such as a sewing cuff 18, a coring tool 21 for removal of a plug of heart tissue, and a conduit 24, all having at least pertinent portions thereof sealed within an enclosure 27 from which all air is or can be evacuated. The apparatus 15 may be attached to a heart, as shown in FIG. 2, using various surgical approaches. In one preferred approach, related to implantation of an LVAD, the patient's thorax is typically opened at the fifth intercostal space (between the fifth and sixth rib) of the left lateral chest wall. For the human anatomy, this region has good exposure to the left ventricular apex, which is the desired location for attachment of an inflow conduit for an LVAD. The apparatus 15 can then be sewn to the ventricular apex such that the sewing cuff 18 is centered over the region where the conduit 24 should be optimally placed. The placement of the sewing cuff 18 can be key to successful inflow conduit performance as it governs the orientation of the inflow conduit with respect to the left ventricle. Improper alignment, such as the inflow conduit pointing into the septal wall, can increase the likelihood of the interventricular septal wall heart tissue blocking the conduit 24. This phenomenon can cause two serious problems to occur. The first is suction of heart tissue against the mouth of the conduit 24, something that could be quite severe when using a continuous flow pump such as described in U.S. Pat. No. 5,928,131. One aspect of this severity is the level of tissue damage and bruising that can occur to the septal wall of the heart. Instances of tissue ripping free and passing through the pump may also occur. The other serious problem is the negative pressure induced at the pump inlet in a tissue blockage instance, which can cause cavitation of the blood. This, in turn, can lead to hemolysis and adversely affect pump performance. Considering that most developers of ventricular assist devices now target five plus years as the pump life, an ongoing problem due to improper inflow conduit alignment would be unacceptable.

The method of fastening the sewing cuff 18 (and hence the apparatus 15) to the heart can vary. Where a sewing cuff 18 is used as the attachment member, separate sutures spaced around the circumference of the cuff is the conventionally preferred manner and can be done with or without pledgets 34 (devices used to provide added support), as shown in FIG. 2. Pledgets 34, although not required, can provide additional support and prevent the excessive leakage of blood. Various other suture types can be used for fastening the sewing cuff 18, or other attachment member, to the heart, which will be clear to those skilled in the art.

The sewing cuff 18 can preferably be made of a biocompatible material, e.g., surgical fabric, such as felt, Dacron, or expanded teflon, which has an approximate thickness of 2 mm. The shape of the sewing cuff 18 can vary, with an annular form being a presently preferred embodiment. However, other shapes can be devised by those skilled in the art, based upon the needs of the patient. For example, if the patient's heart is substantially more pointed than average, an alternate shape may be needed to prevent buckling of the attachment member around its outer circumference. In this case, a petal arrangement may be preferred, as shown in FIG. 2.

If the apparatus 15 is used in conjunction with a heart assist device such as described in U.S. Pat. Nos. 5,928,131 or 6,066,085, then the sewing cuff 18 may also serve as an apical defibrillation electrode. Previous animal testing has demonstrated that a pair of defibrillation electrodes, one at the heart apex and the other at the base of the heart is efficacious and results in a very low defibrillation energy threshold. Utilizing the sewing cuff 18, or other attachment member, for this dual function can eliminate the need for a separate defibrillating electrode in a heart assist system having defibrillation capability.

Figure 3A:
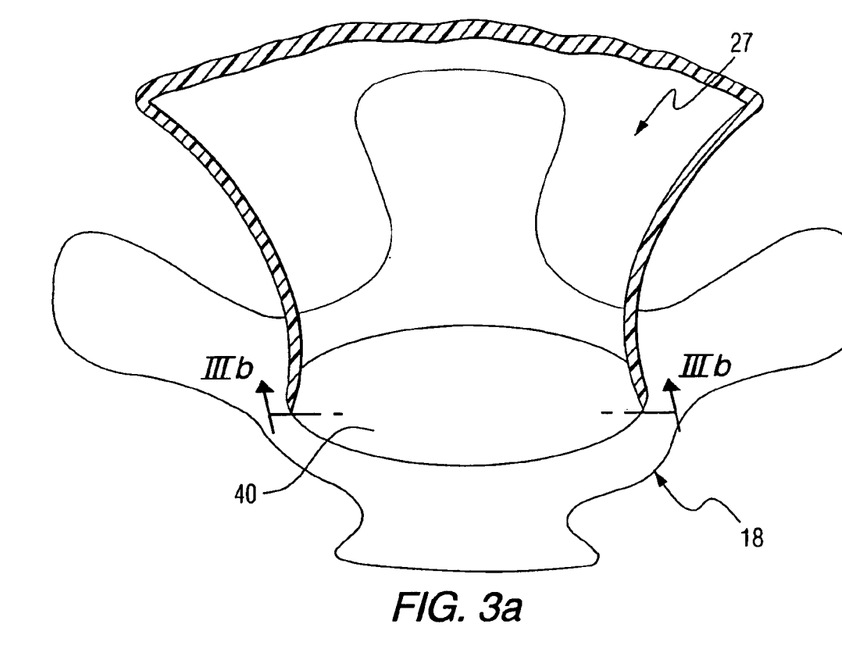
FIG. 3a is a view partially in section of an embodiment of an attachment member for attaching the invention to the ventricle of the heart.
Figure 3B:
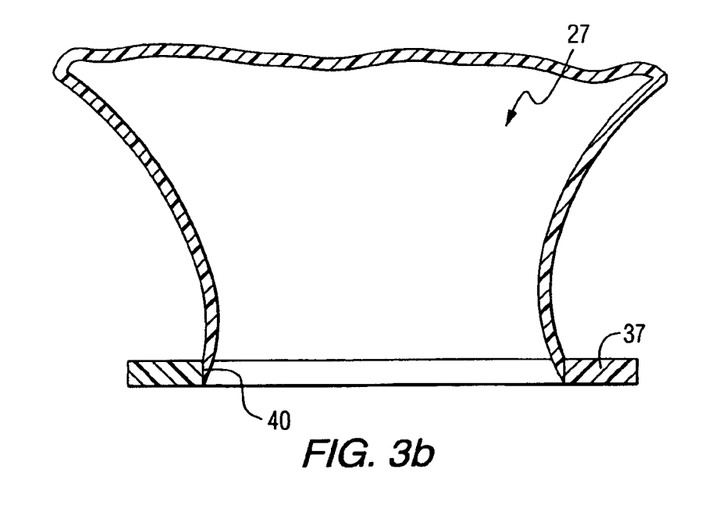
Figure 3C:
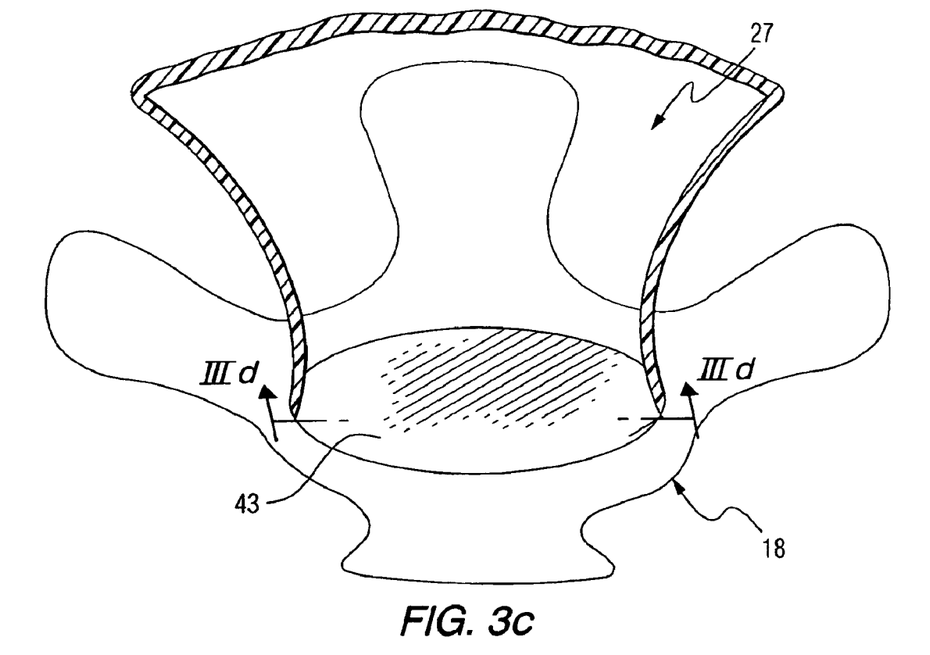
FIG. 3c is a view partially in section of an alternative embodiment of an attachment member for attaching the invention to the ventricle of the heart.
Figure 3D:
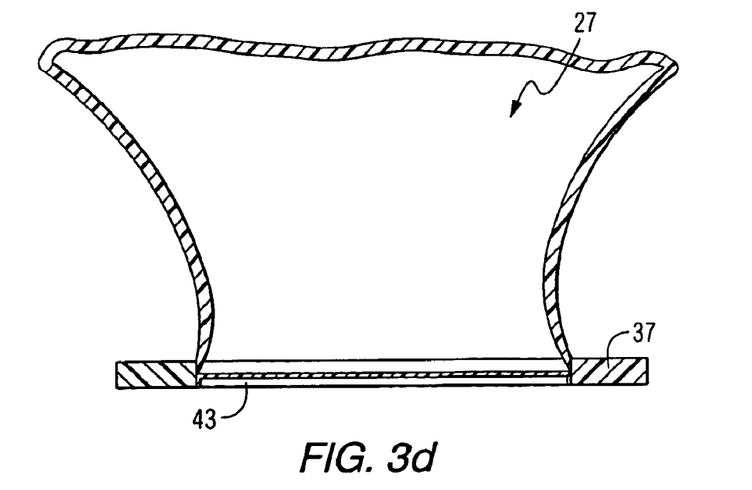
FIG. 3d is a sectional view through line IIId—IIId in FIG. 3c.
Figure 4A:
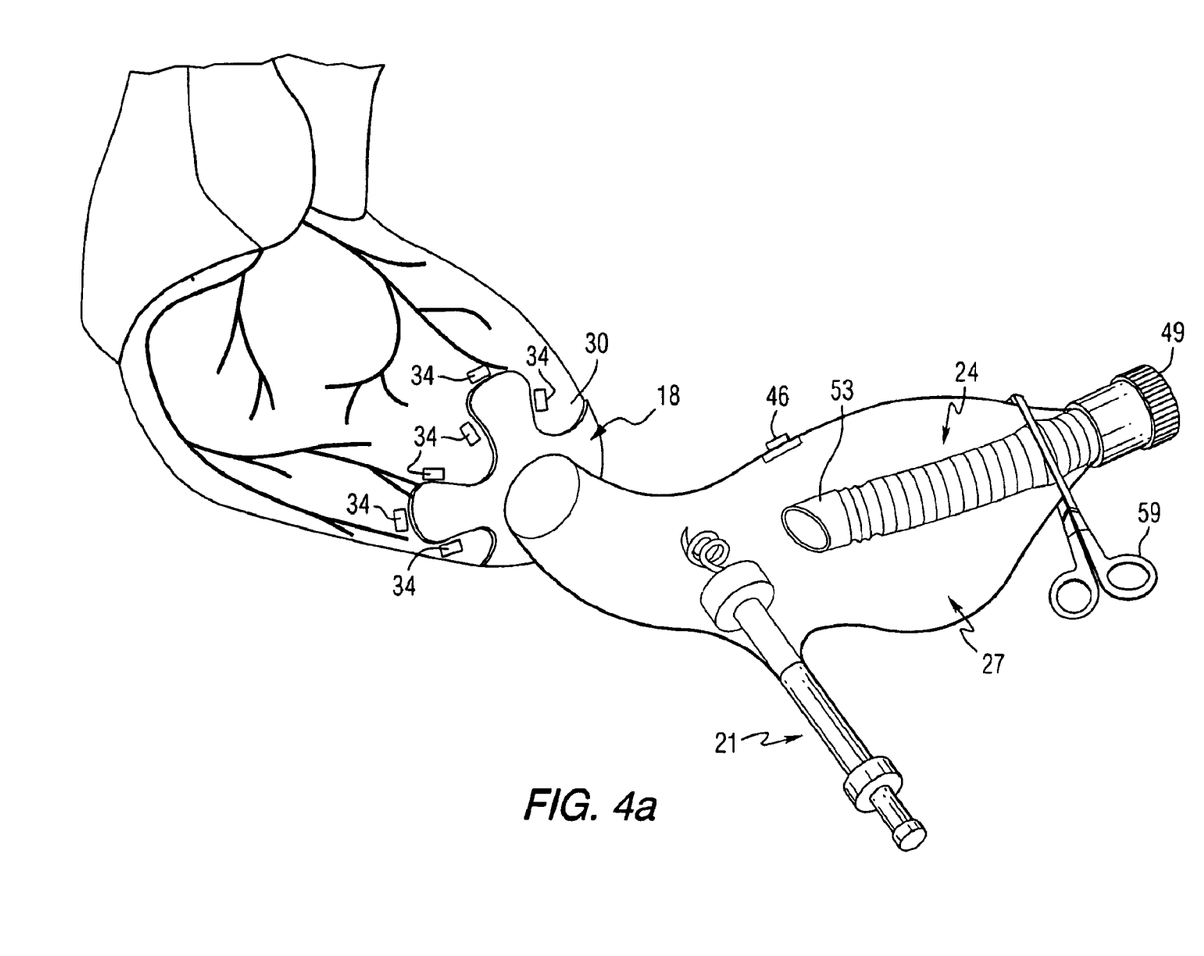
FIG. 4a is a view similar to FIG. 2 showing a manner in which the open end 49 of the conduit 24 can be clamped off to prevent air from entering into the enclosure 27.
Figure 4B:
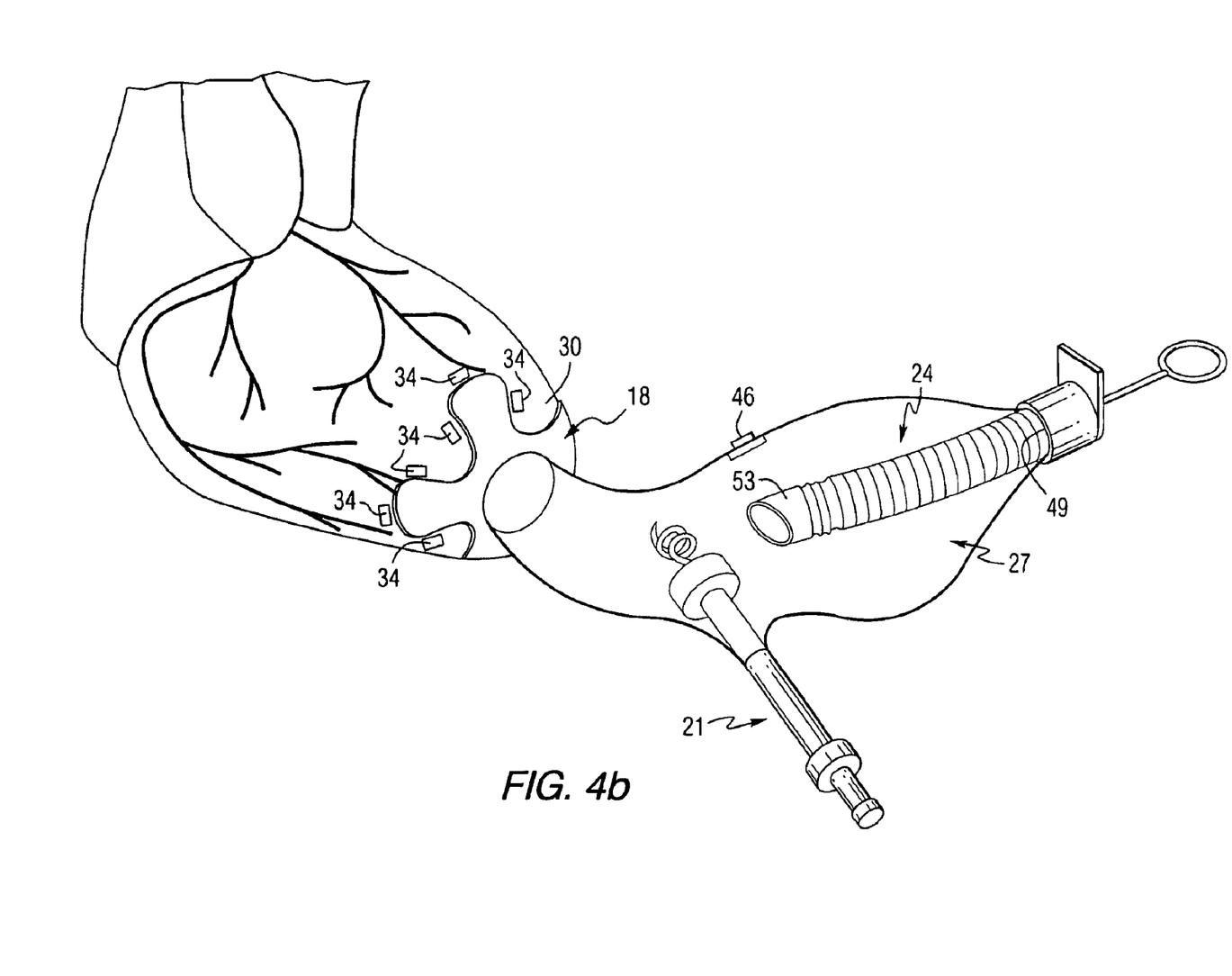
FIG. 4b is a view similar to FIG. 4a showing an alternative manner in which the open end 49 of the conduit 24 may be closed off to prevent air from entering into the enclosing.

The sewing cuff 18 can be attached to the enclosure 27 of the apparatus 15 at the inner circumference of the cuff portion 37, as shown in FIGS. 3a–3d. In one embodiment, the two can be bonded together, as depicted in FIGS. 3b and 3d. Alternatively, a mechanical interlock may be used at this junction. Depending on the needs of the patient, additional cuff material may be used to increase the strength of the bond joint. Additionally, other ways of affixing the sewing cuff 18, or other attachment member, to the heart can easily be conceived by those skilled in the art. The sewing cuff 18, or other attachment member, can have an opening 40 therethrough, as shown in FIGS. 3a and 3b, or can be have a facing 43, as shown in FIGS. 3c and 3d, such that there is no opening 40. Where the sewing cuff 18, and the enclosure 27, have the opening 40 therethrough, the enclosure 27 can be filled with a bio-compatible fluid, such as a sterile saline, after the sewing cuff 18, along with the enclosure 27, is attached to the heart. Alternatively, where the sewing cuff 18 has a facing 43, or if the enclosure 27 is totally enclosed, including where the sewing cuff 18 is affixed, such that the enclosure 27 is pre-sealed prior to attachment of the sewing cuff 18 to the heart, the enclosure 27 can have all air evacuated prior to attachment to the heart. The air can be evacuated, for example, by filling with sterile saline or by a vacuum process. In either case, a fill/empty port 46 can be provided in the enclosure 27 to fill and/or empty the saline, or the saline can be filled/emptied through the conduit 24. In any case, the objective is to remove all air from within the enclosure 27 prior to attaching the conduit 24 to the heart. During a fill procedure, the fill/empty port 46 of the enclosure 27, or open end 49 of the conduit 24, should be kept at the highest level with respect to the floor in order to completely evacuate all of the air from the enclosure 27. Fluid should be added and air removed until the enclosure 27 is completely filled with saline. After all the air has been evacuated, the end 49 of the conduit 24 must be closed temporarily until the enclosed end 53 of the conduit 24 has been installed and secured to the heart and sewing cuff 18. Generally, the conduit 24 is secured to the sewing cuff 18—not to the heart itself. To seal off the connector end of the conduit 24, either an end-cap 56 can be fitted to the connector end of the conduit 24, as shown in FIG. 4b, or the conduit 24 (and any portion of the enclosure 27 adjacent to the conduit 24) may be cross-clamped, such as with clamps 59, to prevent saline from escaping from or air from entering the enclosure 27, as shown in FIG. 4a.

Figure 5:
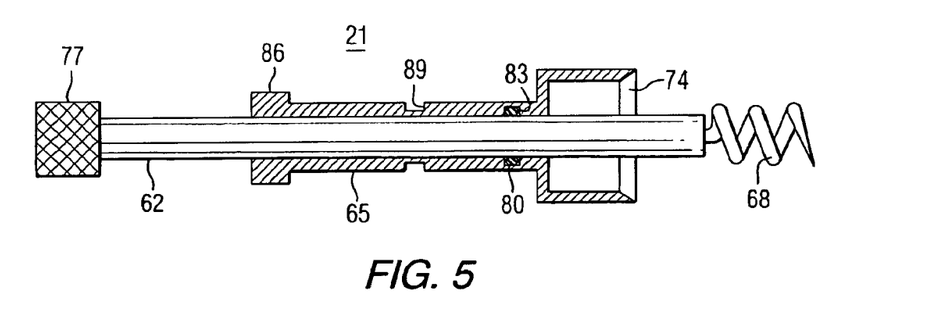
FIG. 5 is a side cross section view of an embodiment of a coring tool.
Figure 6:
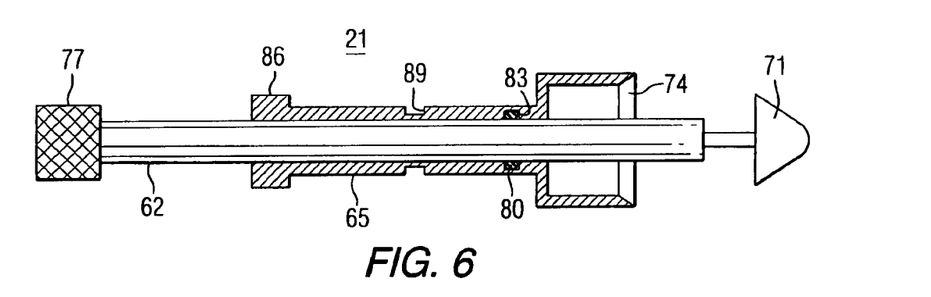
FIG. 6 is a side cross section view of an alternative embodiment of a coring tool.

Once all of the air has been evacuated and the enclosure 27 totally sealed, the coring tool 21, shown in more detail in FIGS. 5 and 6, can be used to remove a section of tissue from the left ventricular apex. The coring tool 21 can have a central rod 62 and an outer tubular barrel 65. The central rod 62 can have a corkscrew-like member 68 for retaining the plug of tissue after it has been cut loose from the heart. Alternatively, if, for example, an initial scalpel incision is made in the left ventricular apex 30, a holding member 71, like that depicted in FIG. 6, could be used. In that case, the holding member 71 would be passed through the incision and into the ventricular cavity, where the tissue can be held from the opposite side while the tissue is cored. Other methods will also be apparent to those skilled in the art. In either case, while the central rod 62 of the coring tool 21 is held stationary, the outer barrel 65 can be rotated as a blade portion 74 of the barrel 65 is pressed against the heart surface. This action is continued until the blade portion 74 of the coring tool 21 barrel 65 passes completely through the heart wall. The entire coring tool and captured tissue plug can then be retracted into the enclosure 27 and kept there while the conduit 24 is being attached to the heart. The size of the enclosure 27 and the coring tool 21 make it possible for arrangement of the inner components of the enclosure 27, such that subsequent manipulations of the conduit 24 within the enclosure 27 are unobstructed by the other enclosed members of the apparatus 15.

Figure 10A:
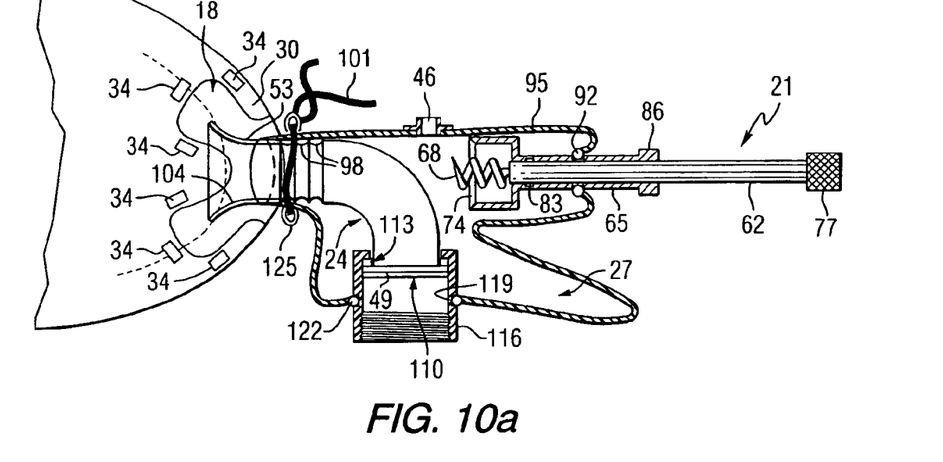
FIGS. 10a and 10b illustrate two different ways in which the attachment member can be secured to the conduit 24.
Figure 10B:
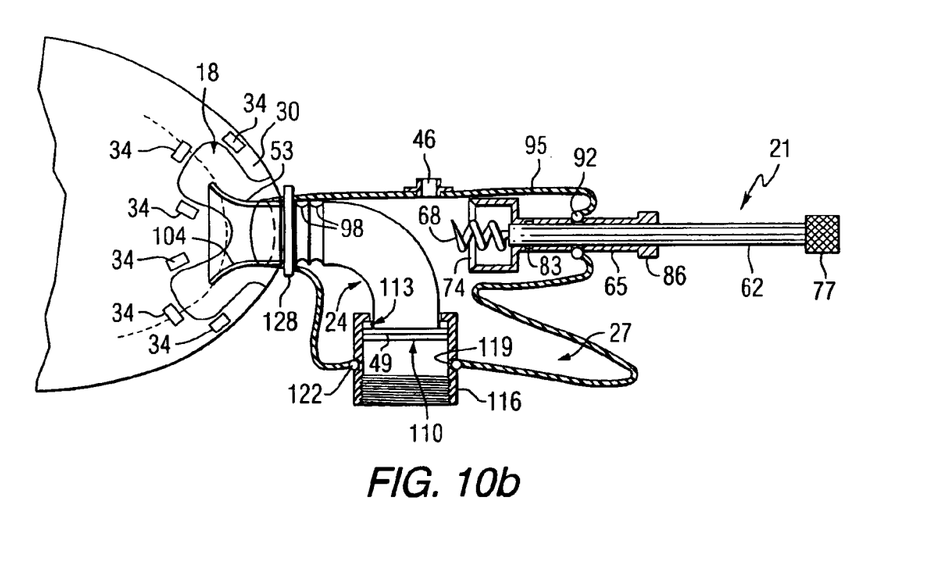

The central rod 62 of the coring tool 21 can have a knurled end 77 for easy manipulation during coring since, in a presently preferred embodiment, the central rod 62 will be held stationary with respect to the barrel 65 during the cutting of the tissue. Near the opposite end of the central rod 62 an O-ring 80 can be provided to seal between the central rod 62 and the barrel 65 while allowing free rotation of the central rod 62 within the barrel 65. The O-ring 80 can be primarily held by a circumferential groove 83 in the barrel 65. Like the end 77 of the central rod 62, a portion 86 of the barrel 65 can also be knurled to aid in manipulation of the barrel 65 during coring. A groove 89 can also be provided in an outer surface of the barrel 65 for accommodation of a sealing bead 92 provided where the enclosure 27 surrounds the barrel 65, as shown in FIGS. 10a–10b. As with the O-ring 80 between the central rod 62 and the barrel 65, the sealing bead 92 between the enclosure 27 and the barrel 65 provides a barrier between the environment within the enclosure and outside the enclosure 27. Alternative sealing methods will also be apparent to those skilled in the art. It should also be noted that the a portion 95 of the enclosure 27, in the region of the sealing bead 92, can be provided with a generally cylindrical shape to facilitate easy gripping of the enclosure 27 and the barrel 65 in that region. The cylindrical cutting edge 74 of the barrel 65 can be of a size which corresponds to the size of conduit 24 being attached. Other embodiments of the coring tool 21 and the sealing methods of the coring tool 21 and enclosure 27 will be apparent to those skilled in the art.

Figure 7:
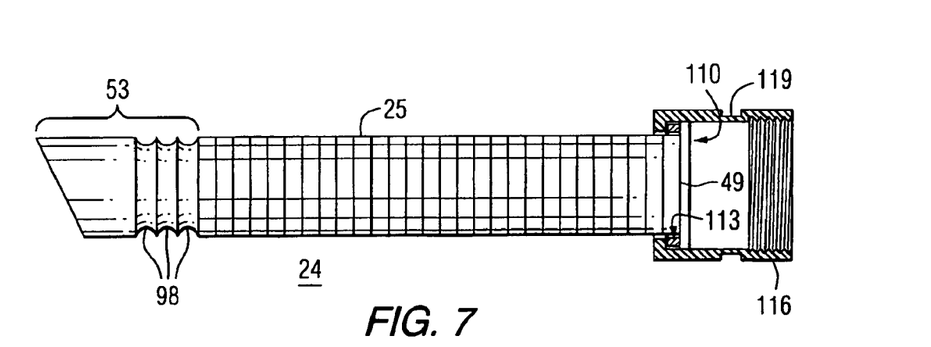
FIG. 7 is a side view of an embodiment of a conduit.
Figure 8A:
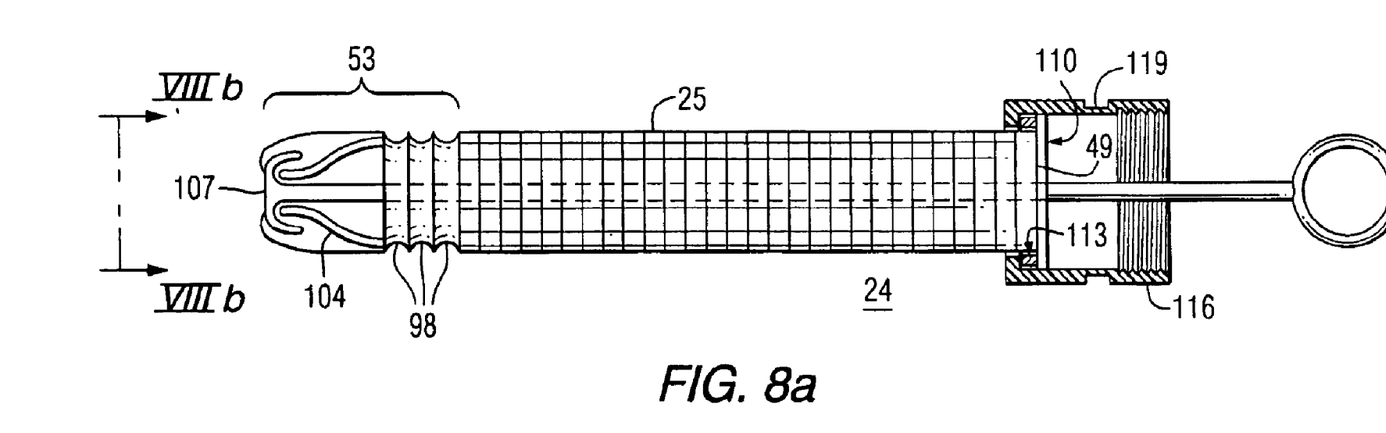
FIG. 8a is a side view of an embodiment of a conduit having an expandable tip.
Figure 8B:
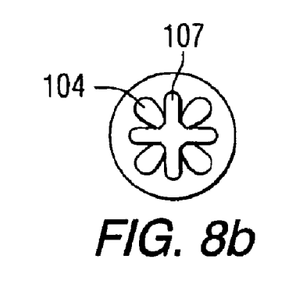
Figures 9A, 9B:
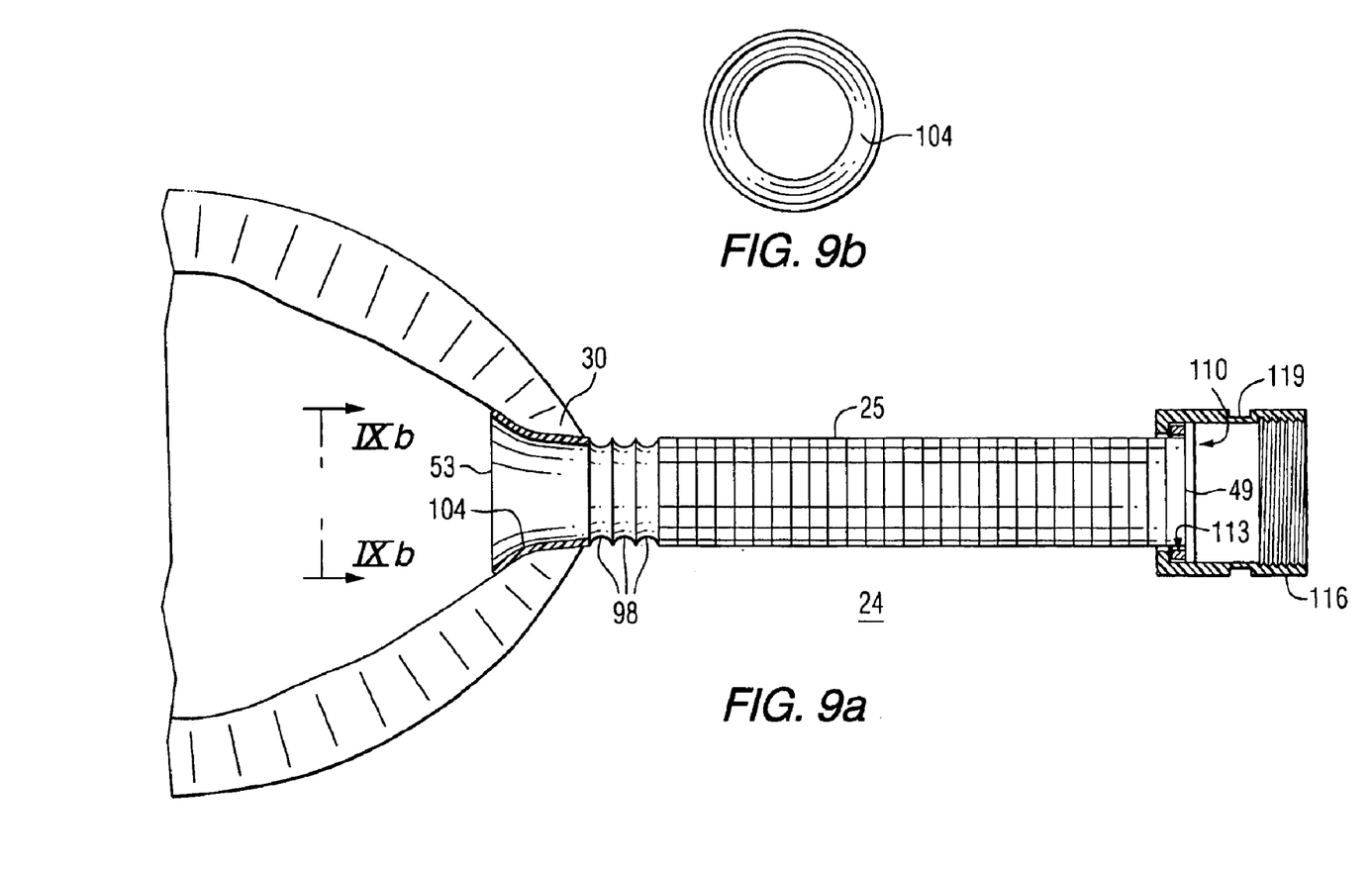

A presently preferred embodiment of the conduit 24 can be as depicted in FIG. 7. The end the conduit 24 which attaches to the ventricular apex may be referred to hereinafter as the apical cannula 53, or simply the cannula 53. The apical cannula 53 may have features that improve alignment within the ventricle, prevent the heart septum from moving over and covering the mouth of the cannula 53, and/or enhance the flow dynamics around and through the cannula 53. In any case the apical cannula 53 can have a provision for attachment to the sewing cuff 18, or other heart attachment member. A series of grooves 98 around the outer circumference of the apical cannula 53 is one such provision. This feature would enable fixation options such as a purse-string type, ligature attachment 101 of the enclosure 27 to the apical cannula 53, as shown in FIG. 10a. One presently preferred apical cannula 53 tip design would be a deployable trumpet tip 104, shown in FIGS. 8a and 8b, which can be expanded into a shape having a minimal pressure drop, good flow dynamics, and which has the capability to support the ventricular wall. In this embodiment, the cannula tip 104 could have a tip holding member 107 to keep the outer maximum diameter of the cannula tip 104 within a dimension that would pass through the hole created in the apex 30 by the coring tool 21. After the tissue plug is removed, the cannula tip 104 could be advanced through the hole, just as in other embodiments, and, after optimum placement, the tip holding member 107 could be advanced to release the trumpeted cannula tip 104 and then withdrawn. The conduit 24 could then be retracted to bring the expanded cannula tip 104 into a snug position against the endocardium of the left ventricle, as shown in FIGS. 9a and 9b. The series of grooves 98 on the cannula facilitate the conduit's ability to permanently have a snug fit regardless of the heart's wall thickness. This feature also prevents the existence of a gap or undercut between the inner wall of the left ventricle and the apical cannula. From a flow standpoint, such a gap or undercut would allow blood to stagnate and potentially cause tissue deposits and the formation of thrombi.

Extending away from the cannula tip 104 can be a vascular graft portion 25 of the conduit 24. A variety of grafts 25 can be used with the invention, but a graft 25 that needs no preclotting is preferable since grafts 25 needing preclotting typically must be thoroughly soaked in the patient's blood before they are installed. Alternatively, a rigid polyurethane portion may be used in place of the vascular graft 25, depending on the needs of the patient. In any case, the nominal diameter of the graft 25, or rigid portion, should match the inner diameter of the apical cannula 53, such that no discontinuity, i.e., step, between the two is present. Such a discontinuity could trigger adverse reactions such as hemolysis and tissue deposits.

Figure 12A:
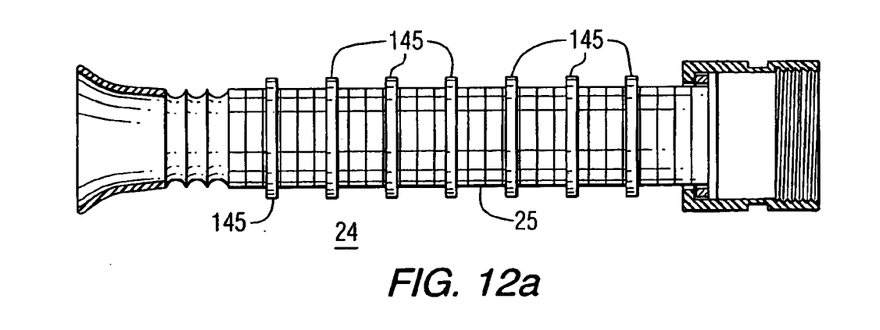
FIG. 12a is a view of the inflow conduit with collapse support rings
Figure 12B:
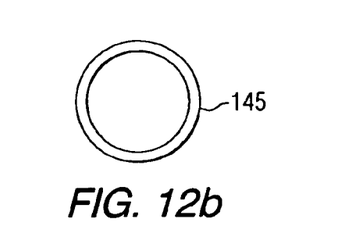

If Dacron or a similar material is used for the vascular graft 25 portion, the inflow conduit 24 may preferably have stiffening washers 25 along the length of graft 25, as shown in FIG. 12. The placement of the washers 25 along the graft 25 portion of the inflow conduit 24 is such that radial and longitudinal stiffness increases while the ability of the conduit 24 to bend is not hampered. In particular, the washers 25 provide a stiffening effect that prevents any collapse of the graft 25 due to bending or due to very low blood pressures within the inflow conduit.

These washers 25 can be made of any material but biocompatible polyurethane is preferred. Their size is mainly governed by the required strength to withstand the low blood pressures within the inflow conduit 24 and any compression from organ-to-organ loads external to the inflow conduit 24. However, the thickness of each washer 25 is kept to a minimum to provide the smallest radial profile that might irritate any tissues the washer 25 may rub against. The edges of the washer 25 are also preferably rounded to prevent any additional tissue irritation. The washers 25 are preferably sized to prevent the collapse of the grafts 25 and must be able to withstand the pull of the graft 25 inward for any low blood pressure conditions within the inflow conduit 24. When Dacron is used, the graft 25 must be rigidly connected to the washers 25 such that the graft 25 will not rip/tear off the washer 25 in any blood pressure related or external loading condition.

The spacing of the washers 25 is such that the prevention of collapse is minimized while the ability of the conduit 24 to bend is maximized. The closer the washers 25 are spaced together, the less likely collapse will occur between them. Conversely, if the washers 25 are spaced too far apart, there exists likelihood that the length of Dacron between the washers 25 will be the primary site for collapse of the conduit 24 due to bending. This spacing also has an affect on the minimum bend radius that is possible for the inflow conduit 24. For the present invention, close spacing is preferred to the extent that a reasonable bend radius is possible for the whole inflow conduit 24. Finally, if the distance between washers 25 is too great, there is also an increased chance of collapse in the unsupported region between the washers 25 due to low blood pressure in the inflow conduit 24.

The extreme opposite end of the vascular graft 25, or rigid portion, can preferably terminate in a flange 110. A washer-like stiffener 113 can be provided adjacent to, and can be bonded to, the flange 110. A threaded shell 116 can be provided which can surround both the end of the conduit 24 and the flange 110, and can be used to fasten the conduit 24 end to an LVAD (not shown). The outside circumference of the threaded shell 116 can have an integral groove 119 that can serve as a locator for a sealing bead 122 of the enclosure 27. The enclosure 27 orifice can be provided with the bead 122 for fluid-tight connection to the threaded shell 116, thus sealing within the enclosure 27 the end of the conduit 24, i.e., the apical cannula 53, which attaches to the sewing cuff 18. Alternative manners of sealing the enclosure 27 about the conduit 24 will also be apparent to those skilled in the art.

The enclosure 27 portion of the apparatus 15, as has been described above, can have four regions associated with enclosing at least portions of the other members of the apparatus 15, e.g., the coring tool 21, sewing cuff 18, conduit 24, and fill/empty port 46 (where provided). In one presently preferred embodiment, the enclosure 27 can preferably be 0.02 inches thick and made of a transparent and durable polymer. The regions associated with the coring tool 21 and the conduit 24 can be provided with orifices having sealing beads 92, 122, as described above, or a similar provision that can preferably be integral to the enclosure 27. This can be important since each of the aforementioned members of the apparatus 15 should be allowed to rotate freely with respect to the enclosure 27 while maintaining an air tight seal. The fill/empty port 46, where provided, can preferably be bonded to the enclosure 27 wall and cannot move relative thereto.

Figure 11A:
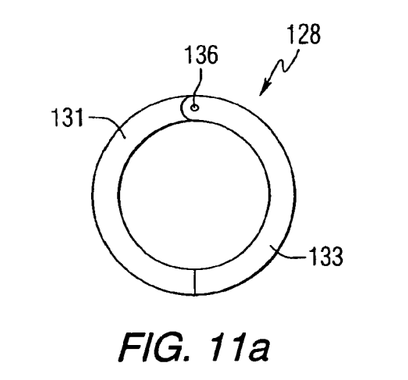
FIGS. 11a through 11c illustrate an embodiment of a clamp, as shown in FIG. 10b, that can be used to secure the attachment member to the conduit 24.
Figure 11B:
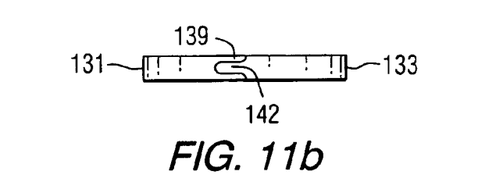
Figure 11C:
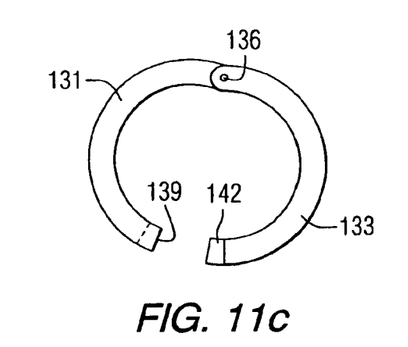

Near the sewing cuff 18 there can be provided a feature for enabling the sewing cuff 18, or other heart attachment member, to be fastened to the apical cannula 53 of the conduit 24. As described previously, one presently preferred embodiment can use a ligature 101 pre-threaded through a tunnel-like passage 125 which can be provided near the sewing cuff 18. After apical cannula 53 placement, the ligature 101 can be tightened and tied off to secure the wall of the enclosure 27 (and hence the sewing cuff 18) to the cannula 53, as shown in FIG. 10a. Alternatively, FIG. 10b illustrates the use of a circular clamp 128 that could be used to capture the enclosure 27 and fasten the attachment member to the apical cannula 53. The plurality of grooves 98 on the apical cannula 53 will allow a proper fit of the apical cannula 53 for various left ventricle muscle wall thicknesses. Those skilled in the art will also recognize other ways to accomplish the same goal. One presently preferred embodiment of a circular clamp 128 is depicted in FIGS. 11a–11c. As shown, the clamp 128 can have a pair of semicircular portions 131,133 which are integrally connected at a central pin 136. The pin 136 allows each semicircular portion 131,133 to be rotated with respect to the other such that the clamp 128 may be opened fully to allow placement around the apical cannula 53 and adjacent enclosure 27. An ample number of grooves 98 can be provided on the apical cannula 53 such that the clamp 128 may be aligned with one of the grooves 98 which provides the optimal positioning relative to the cannula 53. Preferably, each semicircular portion 131,133 of the clamp 128 can have ends 139, 142 configured to clip together opposite the central pin 136. After proper positioning, the clamp 128 is closed to capture the apical cannula 53 and the enclosure 27.

Next, the end 49 of the conduit 24 at the threaded shell 116 side of the cross-clamp 59 can be filled with the sterile saline. Concurrently with the above procedure, an outflow conduit could be sewn to the ascending or descending thoracic aorta using a side-biting clamp (not shown). This outflow conduit can have a connector similar to the inflow conduit connector 116, and both connectors could be attached to opposite ends of a blood pump. Before attachment to the inflow conduit, the blood pump and outflow conduit could also be filled with sterile saline. Then, as the blood pump and the inflow conduit were attached saline could be continually poured onto the connection site to eliminate any possibility of air emboli. Finally, the enclosure 27 can be dissected away from the inflow conduit and the sewing cuff 18.

Figure 13:
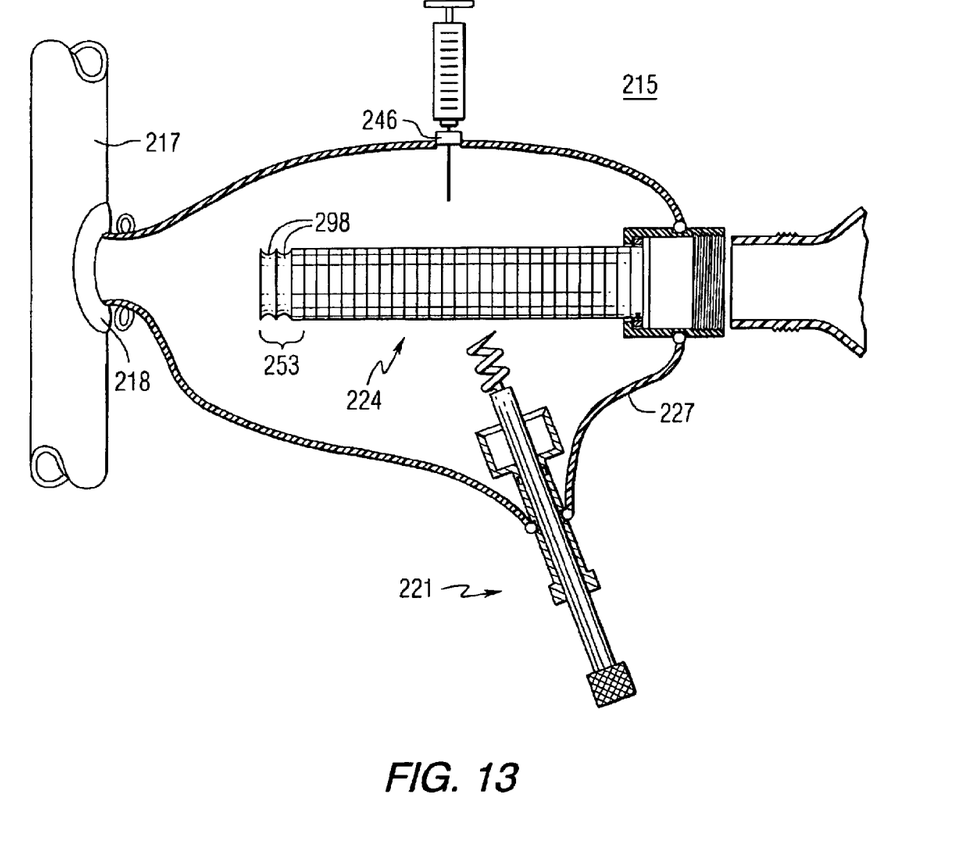
FIG. 13 is a perspective view of an alternative embodiment of the invention as it may look attached a portion of the vasculature other than the heart, such as a large blood vessel like the aorta.

A presently preferred alternative embodiment of the invention is a similar apparatus 215 adapted for safely installing a conduit to other parts of the vasculature, for example a large blood vessel 217, such as an aorta, as illustrated in FIG. 13. Essentially, the apparatus 215 provides for attachment of a conduit to the blood vessel 217 in an air-free environment. The apparatus 215 enables an air-free environment by providing a contained and sealed enclosure 227 around the site intended for the conduit 224 attachment and all instruments required for complete attachment of the conduit 224 to the blood vessel 217. The apparatus 215 can include an attachment member 218, which can be similar to the sewing cuff 18 used in the attachment of the apparatus 15 to the heart ventricle as shown in FIG. 1. The apparatus 215 can further include a coring tool 221 for removal of a plug of tissue from the blood vessel 217, and the conduit 224, each having at least pertinent portions thereof sealed within an enclosure 227 from which all air is or can be evacuated via a fill/empty port 246. The apparatus 215 may be attached to a blood vessel using various surgical approaches well known to those skilled in the art. The apparatus 215 for attaching a conduit 224 to a blood vessel 217 is essentially identical to the apparatus 15 for attaching a conduit to a heart ventricle, with the only difference being the portion(s) of the vasculature to/between which the conduit 24, 224 is attached. However, the defibrillation aspect of the sewing cuff 18 can be eliminated from the sewing cuff 218 in this embodiment of the invention. Additionally, the inflow conduit 224 would not require an apical tip portion like the end of the cannula 53 which attaches to the heart ventricle. Nevertheless, the conduit 224 can include grooves 298, or like features, for the purpose of adjustably locating the conduit 224 with respect to the enclosure 227. Similar to the grooves 98 of the apparatus 15, the grooves 298 of the apparatus 215 enable a ligature or circular clamp to fasten the conduit 224 to the enclosure.

Although certain embodiments of the invention have been described in detail, it will be appreciated by those skilled in the art that various modifications to those details could be developed in light of the overall teaching of the disclosure. As such, those particular embodiments which are disclosed herein should be treated as illustrative only, and not as limiting the scope of the invention, which should be awarded the full breadth of the following claims and any and all embodiments thereof.

What is claimed is:

1. A method of attaching a conduit to a wall of at least one of a heart and a blood vessel, said method comprising:
    a. attaching an attachment portion of an enclosure to said wall;
    b. enclosing within said enclosure at least a first portion of a tool for creating an opening through said wall;
    c. enclosing at least one end of said conduit within said enclosure;
    d. evacuating air from said enclosure;
    e. creating said opening through said wall using said tool;
    f. securing said one end of said conduit to said attachment portion; and
    g. separating said attachment portion from a remainder of said enclosure such that said remainder is removable after said conduit is secured to said attachment portion.

2. The method of claim 1 further comprising filling said enclosure with fluid to evacuate said air.

3. The method of claim 1 further comprising entirely sealing said enclosure prior to attachment to said wall.

4. The method of claim 3 further comprising:
    a. first evacuating air from said enclosure; and
    b. subsequently attaching said enclosure to said wall.

5. The method of claim 4 further comprising filling said enclosure with fluid to evacuate said air.

6. The method of claim 1 further comprising:
    a. providing an opening through said attachment member and said enclosure;
    b. thereafter attaching said attachment member to said wall; and
    c. subsequently evacuating air from said enclosure.

7. The method of claim 6 further comprising filling said enclosure with fluid to evacuate said air.

8. An apparatus for attaching a conduit to a wall of at least one of a heart and a blood vessel, said apparatus comprising:
    a. a sealed enclosure having air evacuated therefrom, said sealed enclosure having an attachment portion adapted for attachment to said wall, said attachment portion detachable from a remainder of said sealed enclosure;
    b. a tool having a first portion for creating an opening through said wall, said first portion contained within said sealed enclosure; and
    c. a conduit having a first end attachable to said attachment portion, said first end contained within said sealed enclosure.

9. The apparatus of claim 8 further comprising said sealed enclosure being filled with fluid.

10. The apparatus of claim 8 wherein said attachment portion further comprises a sewing cuff.

11. The apparatus of claim 8 further comprising a port in said enclosure for evacuating air from said enclosure.

12. The apparatus of claim 8 further comprising said tool having a second portion external to said enclosure, said second portion manipulable to cause said first portion to create said opening.

13. The apparatus of claim 8 wherein said first portion further comprises a holding member.

14. The apparatus of claim 8 wherein said tool further comprises:
    a. a central rod member having a holding member at said first portion of said tool contained within said enclosure;
    b. a barrel member rotatably surrounding said central rod portion, said barrel member having a cutting blade at said first portion of said tool contained within said enclosure;
    c. said central rod member manipulable to engage said holding member with tissue to be cut away by said cutting blade; and d. said barrel member manipulable to cause said cutting blade to cut away tissue to create said opening.

15. The apparatus of claim 8 further comprising said enclosure sealed around said barrel member in a manner permitting rotation of said barrel member.

16. The apparatus of claim 8 further comprising said conduit having a second end external to said enclosure.

17. The apparatus of claim 16 wherein said first end is adapted for attachment to a heart and further comprising said second end being connectable to a blood pump.

18. The apparatus of claim 16 wherein said first end is adapted for attachment to a blood vessel at a first location and further comprising said second end being connectable to said blood pump.

19. A method of attaching a conduit to a wall of at least one of a heart and a blood vessel, said method comprising:

a. evacuating air from a sealed enclosure;

b. enclosing within said sealed enclosure at least a portion of a tool used for creating an opening through said wall;

c. enclosing an end of a conduit within said sealed enclosure;

d. attaching a portion of said sealed enclosure to said wall;

e. creating said opening in said wall using said tool; and f. attaching said end of said conduit at said opening to said portion of said sealed enclosure; and g. separating a remainder of said sealed enclosure from said portion thereof attached to said wall.

20. The method of claim 19 further comprising filling said enclosure with fluid to evacuate said air.

\* \* \* \* \*